(12) United States Patent
Matsushita (10) Patent No.: US 10,932,997 B2
(45) Date of Patent: Mar. 2, 2021

(54) AQUEOUS SKIN CARE AGENT

(71) Applicant: MTG Co., Ltd., Nagoya (JP)

(72) Inventor: Tsuyoshi Matsushita, Nagoya (JP)

(73) Assignee: MTG Co., Ltd., Nagoya (JP)

( * ) Notice: Subject to any disclaimer, the term of this patent is extended or adjusted under 35 U.S.C. 154(b) by 222 days.

(21) Appl. No.: 15/100,169

(22) PCT Filed: Nov. 17, 2014

(86) PCT No.: PCT/JP2014/080308
§ 371 (c)(1),
(2) Date: May 27, 2016

(87) PCT Pub. No.: WO2015/079942
PCT Pub. Date: Jun. 4, 2015

(65) Prior Publication Data
US 2018/0168953 A1    Jun. 21, 2018

(30) Foreign Application Priority Data
Nov. 29, 2013 (JP) .............................. JP2013-247667

(51) Int. Cl.
*A61K 8/19* (2006.01)
*A61K 8/34* (2006.01)
(Continued)

(52) U.S. Cl.
CPC .............. *A61K 8/19* (2013.01); *A61K 8/0241* (2013.01); *A61K 8/345* (2013.01); *A61Q 19/00* (2013.01);
(Continued)

(58) Field of Classification Search
CPC ................ C07K 16/32; A61K 47/6889; A61K 47/6803; A61K 47/6851; A61K 8/19;
(Continued)

(56) References Cited

U.S. PATENT DOCUMENTS 4,046,591 A    9/1977  Laguerre
5,215,782 A    6/1993  Yoshioka et al.
(Continued)

FOREIGN PATENT DOCUMENTS

CN    105188640 A    12/2015
CN    105189362 A    12/2015
(Continued)

OTHER PUBLICATIONS

JP2004224782 english translation (Year: 2004).*
(Continued)

*Primary Examiner* — Aradhana Sasan
*Assistant Examiner* — Quanglong N Truong
(74) *Attorney, Agent, or Firm* — Oblon, McClelland, Maier & Neustadt, L.L.P.

(57) ABSTRACT

An aqueous skin care agent 1 contains 4 to 85 mass % of water, 13 to 80 mass % of a magnetic powder and a thickener. The magnetic powder contains a ferromagnetic ferrite as a main component and has a mean volume particle diameter being 20 to 100 μm as determined from a particle size distribution obtained by a laser diffraction scattering method. The aqueous skin care agent 1 may contain a beauty component such as an iontophoretic component 3 and preferably contain 10 to 45 mass % of glycerin as the thickener.

11 Claims, 1 Drawing Sheet

(51) Int. Cl.
*A61K 8/02* (2006.01)
*A61Q 19/00* (2006.01)
*A61Q 19/10* (2006.01)

(52) U.S. Cl.
CPC ........ *A61Q 19/10* (2013.01); *A61K 2800/412* (2013.01); *A61K 2800/47* (2013.01); *A61K 2800/48* (2013.01)

(58) Field of Classification Search
CPC .. A61K 8/345; A61K 8/0241; A61K 2800/48; A61K 2800/412; A61K 2800/47; A61K 8/34; A61Q 19/00; A61Q 19/10
See application file for complete search history.

(56) References Cited

U.S. PATENT DOCUMENTS

| | | | |
|---|---|---|---|
| 5,989,569 A | | 11/1999 | Dirksing et al. |
| 2005/0232955 A1 | | 10/2005 | Maor et al. |
| 2007/0051276 A1 | * | 3/2007 | Mleczko ............... C09C 1/24 106/456 |
| 2008/0167420 A1 | * | 7/2008 | Inaba ............... C08F 257/02 524/556 |
| 2010/0041903 A1 | | 2/2010 | Yamazaki et al. |
| 2010/0210499 A1 | | 8/2010 | Allef et al. |
| 2011/0223223 A1 | * | 9/2011 | Murata ............... A61K 8/0254 424/401 |
| 2011/0293543 A1 | * | 12/2011 | Yu ............... A61K 8/37 424/59 |
| 2016/0038383 A1 | | 2/2016 | Matsushita et al. |

FOREIGN PATENT DOCUMENTS

| | | | | |
|---|---|---|---|---|
| CN | 106102824 A | | 11/2016 | |
| EP | 2384735 A2 | * | 11/2011 | ............... A61K 8/19 |
| EP | 3 088 042 A1 | | 11/2016 | |
| JP | 61-3765 B2 | | 2/1986 | |
| JP | 64-68313 A | | 3/1989 | |
| JP | 7-324015 A | | 12/1995 | |
| JP | 2004-155720 A | | 6/2004 | |
| JP | 2004-224782 A | | 8/2004 | |
| JP | 2006-124322 A | | 5/2006 | |
| JP | 2010-248170 A | | 11/2010 | |
| RU | 2 434 634 C1 | | 11/2011 | |
| WO | 2008/001553 A1 | | 1/2008 | |
| WO | 2014/156804 A1 | | 10/2014 | |
| WO | 2014/156805 A1 | | 10/2014 | |

OTHER PUBLICATIONS

International Search Report dated Feb. 17, 2015, in PCT/JP2014/080308 Filed Nov. 17, 2014.
Combined Chinese Office Action and Search Report dated Jul. 23, 2018 in corresponding Chinese Patent Application No. 201480065160.2 (with English Translation), 24 pages.
Extended European Search Report dated Apr. 4, 2017 in Patent Application No. 14866078.0.
Joanne Nikitakis, et al., "Glycerin" International Cosmetic Ingredient Dictionary and Handbook, XP002768434, vol. 1, Fifteenth Edition, 2014, pp. 1359-1360 with cover pages.
"Ferrite (magnet)" Wikipedia, the free encyclopedia, https://en.wikipedia.org/w/index.php?title=Ferrite_(magnet)&oldid=604938602, XP055269091, Apr. 19, 2014, pp. 1-4.
Office Action dated Nov. 26, 2018 in Taiwanese Patent Application No. 103140486 (with English translation).
Combine Russian Federation Office Action and Search Report dated Jun. 28, 2018 in Patent Application No. 2016125753/15(040242) (with English translation), 15 pages.
Office Action dated Aug. 31, 2018 in European Patent Application No. 14 866 078.0.
Office Action dated Apr. 25, 2018 in Taiwanese Patent Application No. 103140486 (with English language translation and English translation of categories of cited documents).
Japanese Office Action dated Jul. 3, 2018 in Patent Application No. 2014-242006 (with English translation), 8 pages.
Japanese Office Action dated Jul. 3, 2018 in Patent Application No. 2015-550646 (with English translation), 8 pages.
Office Action as received in the corresponding European Patent Application No. 14 866 078.0 dated Apr. 8, 2019.
Second Office Action as received in the Chinese Patent Application No. 201480065160.2 dated Apr. 12, 2019 w/English Translation.
Korean Office Action dated Mar. 5, 2020 in Korean Patent Application No. 10-2016-7017414 (with unedited computer generated English translation), 11 pages.

* cited by examiner

AQUEOUS SKIN CARE AGENT

TECHNICAL FIELD

The present invention relates to an aqueous skin care agent.

BACKGROUND ART

As a skin care agent used for skin beauty, there is a skin care agent for removing e.g., dirt and waste of the skin by applying the skin care agent to the skin, leaving the agent as it is for a while and removing the agent together with the dirt and waste. Methods for removing such a skin care agent from a skin conventionally range from wiping with e.g., cotton to washing away with e.g., warm water. Recently, easier methods than these conventional ones have been desired for removing a used skin care agent.

For example, Patent Document 1 proposes a skin cleaning cream prepared by adding a powder containing magnetized particles or particles that can be magnetized to an excipient serving as an application base. The skin cleaning cream is, for example, used as follows: after a skin cleaning cream is applied to the skin, a magnet or the like is allowed to approach the skin cleaning cream on the skin surface. Therefore, a magnetic force acts on the powder contained in the skin cleaning cream and the powder is attracted by the magnetic force. Subsequently, the used skin cleaning cream, skin dirt and others attached to the powder are attracted and removed from the skin surface together with the powder. In this manner, the skin cleaning cream is easily removed from the skin surface.

In the meantime, it is also effective for beautifying a skin to apply a cosmetic lotion containing a beauty component and allow the beauty component to infiltrate into the skin after removing skin dirt and others by use of the skin care agent.

PRIOR ART DOCUMENT

Patent Document

Patent Document 1: JP-B-61-3765

SUMMARY OF THE INVENTION

Problem to be Solved by the Invention

However, the skin cleaning cream described in Patent Document 1 uses an excipient which contains an oily ingredient such as Vaseline as a main component. Because of this, the oily ingredient at least partly remains on the skin surface and forms an oil film after the skin cleaning cream is attracted and removed from the skin by the magnetic force. The oil film formed on the skin surface inhibits infiltration of a beauty component contained in a cosmetic lotion into the skin and serves as a factor reducing a beauty effect. Accordingly, it is necessary for the user to additionally wash the face in order to remove the oil film, which makes the user feel annoyed to no small extent.

In contrast, an aqueous skin care agent rarely forms the aforementioned oil film on a skin surface. Accordingly, it is conceivable that a magnetic powder is added to an aqueous skin care agent in order to avoid the aforementioned problem. However, in the case of adding a magnetic powder to an aqueous skin care agent, it is difficult to obtain a paste-like skin care agent suitable for applying to the skin. Such a problem notably occurs as the content of a magnetic powder increases. For example, if the content of a magnetic powder is larger than 13 mass %, it is extremely difficult to disperse the magnetic powder in a skin care agent and substantially impossible to obtain a paste-like skin care agent.

The present invention has been made in view of the aforementioned background and is directed to providing an aqueous skin care agent having excellent performance.

Means for Solving the Problem

According to an aspect of the present invention, there is provided an aqueous skin care agent containing
4 to 85 mass % of water,
13 to 80 mass % of a magnetic powder, and
a thickener,
in which the magnetic powder contains a ferromagnetic ferrite as a main component and has a mean volume particle diameter being 20 to 100 μm as determined from a particle size distribution obtained by a laser diffraction scattering method.

Effects of the Invention

The aqueous skin care agent contains water in a specific amount as mentioned above, a magnetic powder in a specific amount as mentioned above and a thickener. The magnetic powder contains a ferromagnetic ferrite as a main component and has a mean volume particle diameter within a specific range as mentioned above. With this constitution, the magnetic powder is dispersed in the aqueous skin care agent, and the aqueous skin care agent becomes a paste-like appearance suitable for applying to the skin. In addition, when a magnet or the like is allowed to approach the aqueous skin care agent applied to the skin, the magnetic force acts on the magnetic powder and the used aqueous skin care agent containing the magnetic powder can be attracted and removed from the skin surface together with skin dirt and others.

Since the magnetic powder contains an iron oxide, i.e., a ferrite, as a main component, a variation in magnetic properties and color tone is small. Accordingly, a variation in ease of attraction and removal of the aqueous skin care agent and color tone of the aqueous skin care agent can be reduced. In addition, further oxidization of the above magnetic powder rarely occurs in an aqueous skin care agent. For the reason, even if the aqueous skin care agent is stored for a long term, the magnetic property or the like of the magnetic powder rarely changes and performance rarely deteriorates.

Since the aqueous skin care agent is aqueous, an oil film is rarely formed on the skin surface after the used aqueous skin care agent is attracted and removed.

Accordingly, the user can apply a cosmetic lotion or the like directly to the skin surface after the aqueous skin care agent is attracted and removed from the skin surface and does not need to additionally wash the face before a cosmetic lotion or the like is applied. As a result, the aqueous skin care agent simplifies a process for obtaining a beauty effect and can be easily handled by the user.

As mentioned above, the aqueous skin care agent can remove skin dirt and others, has excellent storage stability and further enables to simplify the process for obtaining a beauty effect. Likewise, the above skin care agent has excellent performance.

MODE FOR CARRYING OUT THE INVENTION

In the aqueous skin care agent, the more the content of a component insoluble in water decreases, the more difficult the oil film is formed on a skin surface. The resultant aqueous skin care agent is likely to have excellent performance. Accordingly, it is specified that the aqueous skin care agent is constituted of 50 mass % or more of water along with a water soluble component(s) based on the total content as 100 mass % of components excluding the magnetic powder. In order to suppress formation of an oil film on a skin surface, the content of water and a water soluble component is preferably 60 mass % or more and more preferably 70 mass % or more.

The content of water relative to the whole aqueous skin care agent is 4 to 85 mass %. If the content of water falls within a specific range as mentioned above, the aqueous skin care agent is obtained in a smooth paste-like appearance, in which the magnetic powder is dispersed. As a result, the aqueous skin care agent is easily spread over when applied to the skin and the user feels smooth spreading over the skin.

If the content of water is less than 4 mass %, the aqueous skin care agent is lack of water and formed into a sticky mass. In this case, the user feels rough when the aqueous skin care agent is brought into contact to the skin. In some cases, the aqueous skin care agent may cause an extremely strong stimulation to the skin. Consequently, it becomes difficult to spread the aqueous skin care agent over the skin. To obtain an aqueous skin care agent having a paste-like appearance suitable for application to the skin, it is specified that the content of water is 4 mass % or more. From the same point of view, the content of water is preferably 5 mass % or more and more preferably 6 mass % or more.

In contrast, if the content of water exceeds 85 mass %, it is difficult to obtain an effect of increasing viscosity by the thickener, with the result that the viscosity of the aqueous skin care agent is extremely reduced. In this case, the amount of magnetic powder contained in the aqueous skin care agent to be applied to a skin surface becomes insufficient due to precipitation of the magnetic powder by gravity. If the amount of magnetic powder is insufficient, the magnetic force acting on the whole magnetic powder becomes insufficient when a magnet or the like is allowed to approach, with the result that it becomes difficult to attract and remove the used aqueous skin care agent from a skin surface. Also in this case, due to low viscosity, the aqueous skin care agent drips from the skin surface, and the aqueous skin care agent is hardly applied to the skin. Thus, in order to obtain an aqueous skin care agent having an appropriately large viscosity, it is specified that the content of water is 85 mass % or less. From the same point of view, the content of water is preferably 73 mass % or less, more preferably, 30 mass % or less and further preferably 15 mass % or less.

In the meantime, the content of the magnetic powder relative to the whole aqueous skin care agent is 13 to 80 mass %. If the content of the magnetic powder falls within a specific range as mentioned above, the magnetic force acting on the whole magnetic powder increases when a magnet or the like is allowed to approach the aqueous skin care agent. As a result, the used aqueous skin care agent can be easily removed from a skin surface together with skin dirt and others.

If the content of the magnetic powder is less than 13 mass %, the magnetic force acting on the whole magnetic powder becomes insufficient due to the low content of the magnetic powder when a magnet or the like is allowed to approach. As a result, it becomes difficult to attract and remove the used aqueous skin care agent from a skin surface and the used aqueous skin care agent is likely to remain on the skin surface. In order to easily attract and remove the aqueous skin care agent from a skin surface, it is specified that the content of the magnetic powder is 13 mass % or more. From the same point of view, the content of the magnetic powder is preferably 15 mass % or more, more preferably 30 mass % or more and further preferably 50 mass % or more.

In contrast, if the content of the magnetic powder exceeds 80 mass %, the aqueous skin care agent is formed into a sticky mass due to insufficient contents of water and a thickener. Because of this, it is difficult to spread the aqueous skin care agent over the skin. Accordingly, in order to obtain the aqueous skin care agent in a paste-like appearance suitable for applying to the skin, it is specified that the content of the magnetic powder is 80 mass % or less. From the same point of view, the content of the magnetic powder is preferably 75 mass % or less and more preferably 70 mass % or less.

The magnetic powder contains a ferromagnetic ferrite as a main component. The "main component" herein refers to a compound contained in the largest amount. The magnetic powder usually contains, other than a ferromagnetic ferrite serving as a main component, e.g., an iron-based oxide such as wustite and hematite each having a different degree of oxidation and inevitable impurities.

Examples of the ferromagnetic ferrite include a spinel ferrite, a magneto-plumbite ferrite, a garnet ferrite, a perovskite ferrite and so on. Of these ferrites, a soft ferrite high in saturation magnetization and low in both residual magnetization and magnetic coercive force is preferably contained as a main component of the magnetic powder. Examples of the soft ferrite include a spinel ferrite having a formula represented by $(MO)_x(Fe_2O_3)_y$ (where $x+y=100$ mol %, M is one or two or more elements selected from metallic elements e.g., Fe, Mn, Mg, Sr, Ca, Ba, Cu, Zn, Ni, Li and Co). Of the spinel ferrites, a ferrite having high saturation magnetization is preferably used.

In the magnetic powder to be used in the aqueous skin care agent, the number of the elements constituting a ferrite serving as a main component is preferably small. Thus, Magnetite ($Fe_3O_4$) having high saturation magnetization and constituted of two elements, Fe and O, is further preferably contained as a main component of the magnetic powder.

The mean volume particle diameter of the magnetic powder is specified to be 20 to 100 μm. In this case, it is possible to easily attract and remove the aqueous skin care agent from a skin surface by a magnetic force. The mean volume particle diameter of the magnetic powder can be calculated in terms of 50% cumulative particle diameter (median diameter) obtained in the volume distribution mode in under-sieve representation of the particle size distribution obtained by the laser diffraction scattering method.

If the mean volume particle diameter is less than 20 μm, the particle size distribution of the magnetic powder tends to have a distribution pattern in which the content of an excessively small particle diameter is large. The magnetic force acting on each of the particles decreases as the size of the particle reduces. Because of this, particles having an excessively small particle diameter are difficult to be attracted by a magnet or the like and tend to remain on a skin surface. Also in this case, the magnetic force acting on the whole magnetic powder becomes weak, with the result that the used aqueous skin care agent is likely to remain on the skin surface.

If the magnetic powder having a large amount of excessively small particle diameter, is mixed in an aqueous skin care agent, a phenomenon where the aqueous skin care agent turns red tends to occur. The mechanism underling the phenomenon is still unknown; however, the phenomenon is conceivably caused because the red brown color of a hematite significantly influences the color of the aqueous skin care agent with an increase in particles having an excessively small particle diameter.

In contrast, if the mean volume particle diameter exceeds 100 μm, the particle size distribution has a distribution pattern in which the content of an excessively large particle diameter. In this case, the user feels rough when the aqueous skin care agent containing the magnetic powder is used. Likewise, the sense of use may deteriorate.

As mentioned above, the aqueous skin care agent having the magnetic powder in which the mean volume particle diameter is controlled to fall within a specific range as mentioned above provides an excellent sense of use, and fine particles contained in the magnetic powder and the used aqueous skin care agent rarely remain on a skin surface. From the same point of view, the mean volume particle diameter of the magnetic powder is preferably 50 to 75 μm.

The thickener has an action of increasing the viscosity of the aqueous skin care agent such that the aqueous skin care agent has an appropriate viscosity. Accordingly, the magnetic powder is easily dispersed in the aqueous skin care agent containing a thickener and a paste-like aqueous skin care agent suitable for applying to the skin is easily obtained. The thickener also has an action of imparting adhesiveness to particles constituting the magnetic powder when applied to the skin. Thus, in the aqueous skin care agent containing a thickener, particles of the magnetic powder are easily adhered to each other, with the result that the used aqueous skin care agent is easily removed from a skin surface in the form of a continuous film. Consequently, the aqueous skin care agent can be easily attracted and removed from the skin surface and the used aqueous skin care agent and fine particles in the magnetic powder rarely remain on the skin surface.

In the case where the aqueous skin care agent does not contain a thickener, some problems occur such as precipitation of the magnetic powder by gravity, dripping of the aqueous skin care agent from a skin surface due to low viscosity because the viscosity of the aqueous skin care agent does not increase. As a result, it is difficult to apply the aqueous skin care agent to the skin.

As the thickener, a conventional thickener for cosmetics can be used such as a glycerin, (acrylates/alkyl acrylate (C10-30)) cross polymer, a cellulose derivative, xanthan gum, guar gum, starch and a derivative thereof, alginate and a derivative thereof, agar, sodium polyacrylate, a carboxyvinyl polymer and bentonite. These thickeners may be used alone or in combination.

The viscosity of the aqueous skin care agent is preferably 9000 mPa·s or more. In this case, when the aqueous skin care agent is applied to the skin, the dispersed state of the magnetic powder is likely to be maintained. Since the amount of magnetic powder contained in the aqueous skin care agent applied to a skin surface is sufficiently large, the magnetic force acting on the whole magnetic powder sufficiently increases when the aqueous skin care agent is attracted and removed by the magnetic force. As a result, the magnetic powder and the used aqueous skin care agent can be easily attracted and removed from a skin surface and the used aqueous skin care agent and fine particles in the magnetic powder rarely remain on a skin surface.

The aqueous skin care agent preferably contains 10 to 45 mass % of glycerin relative to the total aqueous skin care agent, as a thickener. In this case, the adhesive force acting between particles of the magnetic powder increases, a wider and continuous film-like structure tends to be formed when the used aqueous skin care agent is removed from a skin. As a result, the aqueous skin care agent is more easily attracted and removed from a skin surface and the used aqueous skin care agent and others more rarely remain on a skin surface. Since glycerin also has an excellent moisturizing effect, the skin can be effectively moisturized after the aqueous skin care agent is attracted and removed.

The aqueous skin care agent may contain a thixotropic agent for imparting thixotropy. The aqueous skin care agent having thixotropy has a high viscosity in the state where the aqueous skin care agent does not flow during e.g., storage. On the other hand, in the state where the skin care agent flows during e.g., application of the agent to a skin, the viscosity of the aqueous skin care agent decreases. Accordingly, the aqueous skin care agent containing a thixotropic agent in storage is high in viscosity and thus the magnetic powder rarely precipitates. In contrast, when applied to the skin, the aqueous skin care agent is likely to have a suitable viscosity for application. As a result, the aqueous skin care agent is suitably applied to a skin while suppressing precipitation of the magnetic powder.

As the thixotropic agent, a conventional thixotropic agent for cosmetics, such as bentonite, 12-hydroxystearic acid and crystalline cellulose, is used.

The aqueous skin care agent may contain a surfactant. The surfactant has an action of dispersing the magnetic powder in the aqueous skin care agent. Because of this, the magnetic powder is more easily dispersed in the aqueous skin care agent containing a surfactant, and the aqueous skin care agent can be obtained as a smooth paste-like appearance.

As the surfactant, a conventional surfactant for cosmetics can be used such as PEG-7 glyceryl cocoate, polyglyceryl-10 laurate, an alkyl sulfate, an acylamino acid salt, a polyoxyethylene alkyl ether sulfate salt, an alkyl ether phosphate salt, an alkyl polyethylene glycol ether, a glycerol polypropylene glycol ether, an alkyl polyglycerol ether and an ethylene oxide-propylene oxide block copolymer. These surfactants may be used alone or in combination.

Each of the particles constituting the magnetic powder preferably has a resin film on the surface. In this case, a ferrite constituting the magnetic powder rarely comes into direct contact with a substance serving as an oxidant such as water so that the magnetic powder is likely to avoid being further oxidized in the aqueous skin care agent. Accordingly, the aqueous skin care agent can more reduce a variation in ease of attraction and removal, color tone, and so on. For the reason that the magnetic powder is more rarely oxidized in an aqueous skin care agent, the aqueous skin care agent can be stored for a longer term.

As the resin constituting a resin film, an acrylates copolymer, a polyvinyl alcohol, a polyvinyl pyrrolidone, a methoxy ethylene-maleic anhydride copolymer, a cationic cellulose, a polyacrylic ester copolymer, a methacrylic ester copolymer or the like can be used. Also, the resin constituting a resin film may contain a pigment such as titanium oxide in order to control the color tone of the magnetic powder.

The magnetic powder preferably has a mean volume particle diameter being 50 to 75 μm as determined from a particle size distribution obtained by a laser diffraction scattering method, a content of particles with a particle diameter being less than 37 μm of 15 mass % or less, and a content of particles with a particle diameter being 105 μm or more of 5 mass % or less.

The content of particles with a particle diameter being less than 37 μm (hereinafter sometimes referred to as "small-diameter particles") can be measured in terms of, for example, the amount of particles that can pass through a standard sieve having a nominal size of 37 μm (400 meshes).

The content of particles with a particle diameter being 105 μm or more (hereinafter sometimes referred to as "large-diameter particles") can be measured in terms of, for example, the amount of particles that cannot pass through a standard sieve having a nominal size of 105 μm (145 meshes).

As described above, in order to obtain the aqueous skin care agent rarely remaining on a skin surface and providing an excellent sense of use, it is preferable that the particle size distribution of the magnetic powder has a distribution pattern in which the content of particles having an excessively small particle diameter and the content of particles having excessively large particle diameter are both small. Therefore, the mean volume particle diameter of the magnetic powder is more preferably 50 to 75 μm.

However, it is sometimes difficult to sufficiently reduce the content of particles with an excessively small particle diameter only by controlling the mean volume particle diameter to fall within the range of 50 μm or more. Thus, it is important not only to control the mean volume particle diameter to fall within the range of 50 μm or more but also to regulate the content of small-diameter particles to be 15 mass % or less as mentioned above. The content of particles with an excessively small particle diameter can be certainly reduced by regulating the content of small-diameter particles to fall within the range of 15 mass % or less.

Similarly, it is sometimes difficult to sufficiently reduce the content of particles with an excessively large particle diameter only by controlling the mean volume particle diameter to fall within the range of 75 μm or less. Thus, it is important not only to control the mean volume particle diameter to fall within the range of 75 μm or less but also to regulate the content of large-diameter particles to be 5 mass % or less as mentioned above. The content of particles with an excessively large particle diameter can be certainly reduced by regulating the content of large-diameter particles to fall within the range of 5 mass % or less.

As mentioned above, the most suitable particle size distribution in which the content of particles having an optimal diameter is large can be realized not only by controlling the mean volume particle diameter of the magnetic powder to fall within a specific range mentioned above but also by regulating both the content of small-diameter particles and the content of large-diameter particles. The magnetic powder, which is finely and carefully controlled so as to have a particle size distribution as mentioned above, has the most suitable properties as the magnetic powder to be blended in an aqueous skin care agent. Accordingly, the aqueous skin care agent containing such the magnetic powder more rarely remains on a skin surface and provides a more excellent sense of use.

It is preferable that the magnetic powder has a chemical component consisting of 80 mass % or more of magnetite and the balance being wustite, hematite and inevitable impurities. In this case, the ratio of a diamagnetic material in the magnetic powder decreases, and thus the magnetic force acting on the whole magnetic powder increases. As a result, the aqueous skin care agent can be more efficiently attracted and removed. Since the degree of oxidation of wustite is low compared to e.g., magnetite, if the content of wustite is reduced, it is likely to avoid further oxidation of the magnetic powder. Consequently, the performance of the aqueous skin care agent can be stabilized for a long term.

The magnetic powder preferably has a saturation magnetization of 80 $Am^2/kg$ or more. In this case, the magnetization of the magnetic powder can be sufficiently increased and the magnetic force acting on the whole magnetic powder can be further increased. As a result, the aqueous skin care agent can be easily attracted and removed from a skin surface.

The aqueous skin care agent may further contain a beauty component providing a beauty effect on the skin in addition to the aforementioned components. The aqueous skin care agent rarely forms an oil film on a skin surface after the used aqueous skin care agent is attracted and removed, as described above. Thus, the amount of a substance, such as dirt of the skin, waste or an oil film, which inhibits the infiltration of a beauty component, is low on the skin surface after the aqueous skin care agent is attracted and removed. In this state, a beauty component easily infiltrates. The beauty component, which is blended in advance in the aqueous skin care agent, can remain applied onto a skin surface even though the aqueous skin care agent is attracted and removed from the skin surface. Accordingly, the beauty component more easily infiltrates into the skin surface. As a result, the beauty effect of the aqueous skin care agent that the user can feel is likely to be improved.

In this case, application of the aqueous skin care agent to the skin and attracting and removing the aqueous skin care agent by magnetic force are serially performed. Owing to this, attraction and removal of skin dirt and others and infiltration of the beauty component into the skin can be continuously performed, contributing to improvement of use's convenience.

As the beauty component, a whitening component such as an ascorbic acid derivative, kojic acid, arbutin and tranexamic acid; a nutritional component such as an amino acid, a vitamin, a plant extract and a microbially fermented product; a moisturizing component or the like can be used.

The aqueous skin care agent preferably contains a charged iontophoretic component. The iontophoretic component in the aqueous skin care agent is present in an ionized state, then a weak current can be applied to the skin after the aqueous skin care agent is attracted and removed from the skin surface. Owing to the current flow, the charged iontophoretic component migrates into the skin and successfully promoting infiltration of the beauty component into the skin. As a result, the beauty effect that the user can feel is likely to be improved. Note that, in a skin care agent containing an oily ingredient as a main component, it is impossible that current flows through a skin after the skin care agent is attracted and removed.

In the above case, the aqueous skin care agent more preferably contains glycerin together with the iontophoretic component. Since glycerin has an excellent moisturizing action as mentioned above, the aqueous skin care agent having such a composition can retain a large amount of water on a skin surface after the aqueous skin care agent is attracted and removed, compared to the aqueous skin care agent containing no glycerin. As a result, a weak current for promoting infiltration of the iontophoretic component into the skin can easily flow and ions can be easily introduced.

It is preferable that the aqueous skin care agent has an electrical conductivity of 20 μS/cm or more at 25° C. In this case, since a weak current for promoting infiltration of the iontophoretic component into the skin easily flows, ions can be easily introduced.

The aqueous skin care agent may contain additives usually used in cosmetics in addition to the aforementioned components. Examples of the additives include a lubricant, an anti-microbial agent, a fragrance and a pH adjusting agent. These additives can be appropriately added as long as the effects of the present invention are not undermined.

Example

An example of the aqueous skin care agent will be described. The aqueous skin care agent of present example contains 4 to 85 mass % of water, 13 to 80 mass % of a magnetic powder and a thickener, as shown in Table 1 and Table 3. The magnetic powder contains a ferromagnetic ferrite as a main component and has a mean volume particle diameter being 20 to 100 μm determined from a particle size distribution obtained by a laser diffraction scattering method.

Figure 1:
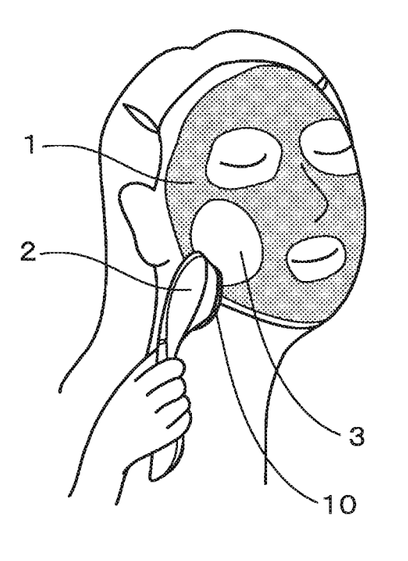
FIG. 1 is a view for explaining how to use an aqueous skin care agent according to Example.

An aqueous skin care agent 1 is applied to the skin and thereafter attracted and removed from the skin surface by allowing a remover 2 containing a magnet to approach the skin, as shown in FIG. 1 (reference symbol 10). The aqueous skin care agent 1 is constituted such that an iontophoretic component 3 remains on the skin surface after the aqueous skin care agent 1 is attracted and removed by magnetic force. Note that, a case where the aqueous skin care agent 1 is applied to the face of a user is shown as an example in FIG. 1; however, the aqueous skin care agent 1 can be used by applying to parts other than the face, including hands, arms, back and so on.

In present example, test agents (test agents 1 to 21) were prepared by mixing individual components in accordance with the ratios shown in Table 1 and Table 3. As the magnetic powder, four types of powders, namely, a magnetite-based magnetic powder, a red oxide powder, a pigment-grade black iron oxide and an iron powder, were used, as shown in Table 1 and Table 3. The preparation method and natures of individual magnetic powders are as follows.

<Magnetite-Based Magnetic Powder>

Preparation Method

A slurry was prepared by adding water to a powder obtained by pulverizing hematite ($Fe_2O_3$), such that a solid content was 55 mass %. Subsequently, 1 mass % of a polyvinyl alcohol relative to the solid content of the slurry, 0.9 mass % of a carbon black and 0.5 mass % of a polycarboxylate salt were added to the resultant slurry. Thereafter, water was added to the mixture to prepare a slurry having 55 mass % of a solid content. Subsequently, the resultant slurry was stirred by use of an attritor for one hour, and then, spherically granulated by use of a spray dryer. The grain sizes of the granules were controlled by a gyro shifter.

The spherical granules controlled in grain size were heated at 1320° C. for 3 hours to reduce a raw-material hematite. In this manner, a calcined product containing magnetite as a main component was obtained. Note that, the granules were heated by use of a tunnel type electric furnace in a nitrogen atmosphere.

The resultant calcined product was pulverized and classified by use of a gyro shifter in combination with an air classifier. In this manner, a particle size distribution was controlled. Thereafter, particles having a large magnetic susceptibility were selected by electromagnetic separation to obtain a magnetite-based magnetic powder.

By performing surface treatment to the resultant magnetite-based magnetic powder as mentioned above, a resin film consisting of an acrylates copolymer was formed on the surface of particles constituting the magnetic powder.

Mean Volume Particle Diameter

The mean volume particle diameter was calculated by the following method. First, a 0.2% aqueous solution of sodium hexametaphosphate was added to the magnetite-based magnetic powder. The resultant mixture was subjected to an ultrasonic treatment using an ultrasonic homogenizer (UH-3C, manufactured by Ultrasonic Engineering Co., Ltd.) for one minute to prepare a dispersion liquid of the magnetite-based magnetic powder. The dispersion liquid was introduced in a micro track particle-size analyzer (Model 9320-X100 manufactured by Nikkiso Co., Ltd.). Analysis was performed in the conditions: a refractive index of 1.81, a temperature of 25±5° C., and a humidity of 55±15%, to obtain a particle size distribution in accordance with the laser diffraction scattering method. From the resultant particle size distribution, a cumulative 50% particle diameter represented in terms of mesh size of sieves with a volume distribution mode, was calculated and employed as a mean volume particle diameter (median diameter).

From the above results, the mean volume particle diameter of the magnetite-based magnetic powder was about 70 μm.

Contents of Small-Diameter Particles and Large-Diameter Particles

A magnetite-based magnetic powder was classified by a method according to JIS H 2601 using the standard sieves specified in JIS Z 8801. In this way, the content of small-diameter particles, namely, particles passed through the standard sieve having a nominal dimension of 37 μm (400 meshes) and the content of large-diameter particles, namely, particles not passed through a standard sieve having a nominal dimension of 105 μm (145 meshes) were measured.

As a result, the content of small-diameter particles in the magnetite-based magnetic powder was 6.7 mass % and the content of the large-diameter particles was 0 mass %.

Saturation Magnetization, Residual Magnetization and Magnetic Coercive Force

Magnetic properties were measured by use of an integral type B-H tracer (Model: BHU-60, manufactured by Riken Denshi Co., Ltd.) in the following procedure. First, an H coil for measuring a magnetic field and a 4πI coil for measuring magnetization were placed between electromagnets and the magnetite-based magnetic powder was put in the 4πI coil. Then, the current values of the electromagnets were changed to vary the magnetic field H. The outputs from the H coil and the 4πI coil were separately integrated. The output from H coil was plotted on the X-axis and the output from the 4πI coil was plotted on the Y-axis. In this manner, a hysteresis loop was drawn on a recording paper. From the hysteresis loop, saturation magnetization, residual magnetization and magnetic coercive force were calculated. Note that, the measurement condition for the hysteresis loop were as follows: sample amount of about 1 g, sample cell of 7 mmφ±0.02 mm in inner diameter and 10 mm±0.1 mm in height, the number of turns of 4πI coil of 30; applied magnetic field of 3000 oersteds.

As a result, the magnetite-based magnetic powder had a saturation magnetization of 82 $Am^2/kg$, a residual magnetization of 82 $Am^2/kg$ and a magnetic coercive force of 24 Oe.

Chemical Components

The composition ratio of magnetite ($Fe_3O_4$), hematite ($Fe_2O_3$) and wustite (FeO) was calculated in accordance with the following method using the X-ray diffraction method.

As a measuring device, "X'PertPRO MPD" manufactured by PANalytical B.V. was used. Measurement was performed using a Co bulb (CoKα beam) as an X-ray source, a centralized optical system as an optical system and a fast detector, "X'Celarator", by continuous scanning at a rate of 0.2°/sec. The measurement results were analyzed by analysis software, "X'PertHighScore" in the same manner as in ordinary crystal structure analysis of a powder to identify a crystal structure. Thereafter, an abundance ratio on a weight basis was calculated by refinement of the obtained crystal structure. Note that, when the abundance ratio of magnetite, hematite and wustite was calculated, Fe and O were regarded as essential elements.

As the X-ray source to be used in the X-ray diffraction measurement, a Cu bulb may be used without a problem; however, in the case of a Fe-rich sample, the background noise becomes large compared to a peak of a measuring target. Thus, a Co bulb is preferably used. Even if collimating optics is used as the optical system, the same results can be obtained; however, X-ray intensity is low and a long time is required for measurement. For this reason, measurement in a centralized optical system is preferable. The speed of the continuous scanning is not particularly limited; however, the intensity of the main peak of magnetite, i.e., the peak in the (311) plane, became 50000 cps or more in order to obtain a sufficient S/N ratio for analyzing a crystal structure. A sample was set in a sample cell such that particles were not preferentially oriented in a specific direction. In this manner, measurement was performed.

As a result, the magnetite-based magnetic powder contained chemical components having 89.7 mass % of magnetite, 4.1 mass % of hematite and 6.2 mass % of wustite.

<Red Iron>

A commercially available pigment-grade red iron ("Tarox R-156L", manufactured by DAITO KASEI KOGYO CO., LTD.) was used. Note that, the mean volume particle diameter of the red iron was 0.1 to 0.6 μm.

<Pigment-Grade Black Iron Oxide>

A commercially available pigment-grade black iron oxide ("Tarox BL-100", manufactured by DAITO KASEI KOGYO CO., LTD.) was used. Note that, the mean volume particle diameter of the pigment-grade black iron oxide was 0.1 to 0.6 μm.

<Iron Powder>

A commercially available iron powder (manufactured by Powdertech CO., LTD.) was used. Note that, the mean volume particle diameter of the iron powder was about 80 μm.

TABLE 1

|  |  | Test Agent 1 | Test Agent 2 | Test Agent 3 | Test Agent 4 | Test Agent 5 | Test Agent 6 | Test Agent 7 | Test Agent 8 |
| --- | --- | --- | --- | --- | --- | --- | --- | --- | --- |
| Water | mass % | 32.92 | 25.42 | 15.42 | 7.92 | 6.42 | 5.92 | 72.12 | 57.12 |
| <Magnetic Powder> |  |  |  |  |  |  |  |  |  |
| Magnetite-Based Magnetic Powder | mass % | 15.0 | 30.0 | 50.0 | 65.0 | 68.0 | 71.0 | 15.0 | 30.0 |
| Red Iron | mass % | — | — | — | — | — | — | — | — |
| Pigment-Grade Black Iron Oxide | mass % | — | — | — | — | — | — | — | — |
| Iron Powder | mass % | — | — | — | — | — | — | — | — |
| <Thickener> |  |  |  |  |  |  |  |  |  |
| Glycerin | mass % | 42.5 | 35 | 25 | 17.5 | 16 | 13.5 | 10 | 10 |
| Sodium Polyacrylate | mass % | 0.01 | 0.01 | 0.01 | 0.01 | 0.01 | 0.01 | 0.01 | 0.01 |
| Carboxyvinyl Polymer | mass % | — | — | — | — | — | — | 0.5 | 0.5 |
| <Surfactant> |  |  |  |  |  |  |  |  |  |
| Polyglyceryl Laurate | mass % | 0.2 | 0.2 | 0.2 | 0.2 | 0.2 | 0.2 | — | — |
| <Iontophoretic Component> |  |  |  |  |  |  |  |  |  |
| Sodium Ascorbyl Phosphate | mass % | 0.1 | 0.1 | 0.1 | 0.1 | 0.1 | 0.1 | 0.1 | 0.1 |
| <Other Additives> |  |  |  |  |  |  |  |  |  |
| Bentonite | mass % | 0.15 | 0.15 | 0.15 | 0.15 | 0.15 | 0.15 | 0.15 | 0.15 |
| Methylparaben | mass % | 0.3 | 0.3 | 0.3 | 0.3 | 0.3 | 0.3 | 0.3 | 0.3 |
| Decamethylcyclopentasiloxane | mass % | 1 | 1 | 1 | 1 | 1 | 1 | — | — |
| Trioctyl Glyceryl | mass % | 3 | 3 | 3 | 3 | 3 | 3 | — | — |
| Cetyl 2-Ethylhexanoate | mass % | 3 | 3 | 3 | 3 | 3 | 3 | — | — |
| Polyoxyethylene · Methyl Polysiloxane Copolymer | mass % | 1.8 | 1.8 | 1.8 | 1.8 | 1.8 | 1.8 | 1.8 | 1.8 |
| Sodium Hydroxide | mass % | 0.02 | 0.02 | 0.02 | 0.02 | 0.02 | 0.02 | 0.02 | 0.02 |

|  |  | Test Agent 9 | Test Agent 10 | Test Agent 11 | Test Agent 12 | Test Agent 13 | Test Agent 14 | Test Agent 15 | Test Agent 16 |
| --- | --- | --- | --- | --- | --- | --- | --- | --- | --- |
| Water | mass % | 22.12 | 28.92 | 32.92 | 6.42 | 6.42 | 6.42 | 15.42 | 25.42 |
| <Magnetic Powder> |  |  |  |  |  |  |  |  |  |
| Magnetite-Based Magnetic Powder | mass % | 65.0 | — | — | — | — | — | — | — |
| Red Iron | mass % | — | 15.0 | 10.0 | 44.0 | 45.0 | — | — | — |
| Pigment-Grade Black Iron Oxide | mass % | — | — | 5.0 | — | 23.0 | 68.0 | 50.0 | 30.0 |
| Iron Powder | mass % | — | 8.0 | — | 24.0 | — | — | — | — |

TABLE 1-continued

| <Thickener> | | | | | | | | | |
|---|---|---|---|---|---|---|---|---|---|
| Glycerin | mass % | 10 | 38.5 | 42.5 | 16 | 16 | 16 | 25 | 35 |
| Sodium Polyacrylate | mass % | 0.01 | 0.01 | 0.01 | 0.01 | 0.01 | 0.01 | 0.01 | 0.01 |
| Carboxyvinyl Polymer | mass % | 0.5 | — | — | — | — | — | — | — |
| <Surfactant> | | | | | | | | | |
| Polyglyceryl Laurate | mass % | — | 0.2 | 0.2 | 0.2 | 0.2 | 0.2 | 0.2 | 0.2 |
| <Iontophoretic Component> | | | | | | | | | |
| Sodium Ascorbyl Phosphate | mass % | 0.1 | 0.1 | 0.1 | 0.1 | 0.1 | 0.1 | 0.1 | 0.1 |
| <Other Additives> | | | | | | | | | |
| Bentonite | mass % | 0.15 | 0.15 | 0.15 | 0.15 | 0.15 | 0.15 | 0.15 | 0.15 |
| Methylparaben | mass % | 0.3 | 0.3 | 0.3 | 0.3 | 0.3 | 0.3 | 0.3 | 0.3 |
| Decamethylcyclopentasiloxane | mass % | — | 1 | 1 | 1 | 1 | 1 | 1 | 1 |
| Trioctyl Glyceryl | mass % | — | 3 | 3 | 3 | 3 | 3 | 3 | 3 |
| Cetyl 2-Ethylhexanoate | mass % | — | 3 | 3 | 3 | 3 | 3 | 3 | 3 |
| Polyoxyethylene · Methyl Polysiloxane Copolymer | mass % | 1.8 | 1.8 | 1.8 | 1.8 | 1.8 | 1.8 | 1.8 | 1.8 |
| Sodium Hydroxide | mass % | 0.02 | 0.02 | 0.02 | 0.02 | 0.02 | 0.02 | 0.02 | 0.02 |

Test agents 1 to 21 shown in Table 1 and Table 3 were evaluated for appearance of a preparation, viscosity, ease of attraction and removal from a skin surface and residual volume on a skin surface in accordance with the following methods. The evaluation results with respect to individual evaluation items are shown in Table 2 and Table 4.

<Appearance of Preparation>

Appearance of preparations of test agents 1 to 21 were visually observed. The results are shown in Table 2 and Table 4. Note that, in Table 2 and Table 4, reference symbols provided in the column of "Appearance of Preparation" individually represent the following states.

A: Test agent shows a smooth paste-like appearance and the user does not feel roughness when the agent is applied to the skin.

B: Test agent shows virtually a paste-like appearance and can be spread over the skin, but the user feels roughness.

C: Test agent shows like a sticky mass and cannot be spread over the skin.

<Viscosity>

Viscosity was measured by a rotational viscometer (Type B viscometer BH, manufactured by TOKYO KEIKI INC.) and the viscosity values obtained are shown in Table 2 and Table 4. Note that, conditions of viscosity measurement are as follows.

Rotor: No. #6
Rotational speed: 20 rpm
Measurement temperature: 25° C.
Measurement time: 60 seconds <Ease of Attraction and Removal>

A test agent was applied to the skin and then allowed to leave as it was for a few minutes. Thereafter, four types of magnets, which had surface magnetic flux density values of 400G, 800G, 1200G and 2800G, respectively, were allowed to approach the test agent applied on the skin. When the distance between the magnet and the skin reached about 10 mm, the attraction state of the test agents was visually observed. The results are shown in Table 2 and Table 4. Note that, in Table 2 and Table 4, the reference symbols provided in the column of "Ease of Attraction and Removal" individually represent the following states.

A: Test agent is attracted and removed in the form of a continuous film.

B: Test agent is attracted and removed in the form of a continuous film; however, the size of the film is smaller than A.

C: Attraction and Removal of a test agent is not completed and the test agent is suspended between the skin and the magnet.

D: Test agent does not respond to the magnet and cannot be attracted and removed.

–: Test agent cannot be applied and any test was not carried out.

<Residual Amount on Skin Surface>

A test agent was applied to the skin and then allowed to leave as it was for a few minutes. Thereafter, four types of magnets, which had surface magnetic flux density value of 400G, 800G, 1200G and 2800G, respectively, were allowed to approach the test agent applied on the skin. When the distance between the magnet and the skin reached about 10 mm, the residual amount of the test agents on the skin surface was visually observed. The results are shown in Table 2 and Table 4. Note that, in Table 2 and Table 4, the reference symbols provided in the column of "Residual Amount on Skin Surface" individually represent the following states.

A: Test agent does not remain on the skin surface.

B: Grain-like test agent remains on about 2 to 3 sites of the skin surface.

C: Test agent remains on a larger number of sites of the skin surface than B.

D: Almost the whole amount of a test agent remains on the skin surface.

–: Test agent cannot be applied and any test was not carried out.

TABLE 2

| | | Test Agent 1 | Test Agent 2 | Test Agent 3 | Test Agent 4 | Test Agent 5 | Test Agent 6 | Test Agent 7 | Test Agent 8 | Test Agent 9 | Test Agent 10 | Test Agent 11 | Test Agent 12 | Test Agent 13 | Test Agent 14 | Test Agent 15 | Test Agent 16 |
|---|---|---|---|---|---|---|---|---|---|---|---|---|---|---|---|---|
| Appearance of Preparation | | A | A | A | A | A | A | A | A | A | A | A | C | C | C | B | A |
| Viscosity (mPa · s) | | 9100 | 15500 | 18600 | 20700 | 21500 | 22300 | 17900 | 16800 | 12600 | 15500 | 18400 | — | — | — | 20300 | 16800 |
| Ease of | 400 G | D | D | D | D | D | D | D | D | D | D | D | — | — | — | D | D |

TABLE 2-continued

| | | Test Agent 1 | Test Agent 2 | Test Agent 3 | Test Agent 4 | Test Agent 5 | Test Agent 6 | Test Agent 7 | Test Agent 8 | Test Agent 9 | Test Agent 10 | Test Agent 11 | Test Agent 12 | Test Agent 13 | Test Agent 14 | Test Agent 15 | Test Agent 16 |
|---|---|---|---|---|---|---|---|---|---|---|---|---|---|---|---|---|---|
| Attraction and Removal | 800 G | B | B | B | B | B | B | B | B | B | D | D | — | — | — | C | C |
| | 1200 G | B | B | A | A | A | A | B | B | A | D | D | — | — | — | C | C |
| | 2800 G | B | B | A | A | A | A | B | B | A | D | D | — | — | — | C | C |
| Residual Amount on Skin Surface | 400 G | D | D | D | D | D | D | D | D | D | D | D | — | — | — | D | D |
| | 800 G | B | B | B | B | B | B | B | B | B | D | D | — | — | — | C | C |
| | 1200 G | B | B | B | B | B | B | B | B | B | D | D | — | — | — | C | C |
| | 2800 G | B | B | A | A | A | A | B | B | A | D | D | — | — | — | C | B |

TABLE 3

| | | Test Agent 17 | Test Agent 18 | Test Agent 19 | Test Agent 20 | Test Agent 21 |
|---|---|---|---|---|---|---|
| Water | mass % | 84.09 | 2.42 | 77.12 | 2.12 | 87.14 |
| <Magnetic Powder> | | | | | | |
| Magnetite-Based Magnetic Powder | mass % | 15.0 | 85.0 | 10.0 | 85.0 | 10.0 |
| Red Iron | mass % | — | — | — | — | — |
| Pigment-Grade Black Iron Oxide | mass % | — | — | — | — | — |
| Iron Powder | mass % | — | — | — | — | — |
| <Thickener> | | | | | | |
| Glycerin | mass % | — | 5 | 10 | 10 | — |
| Sodium Polyacrylate | mass % | — | 0.01 | 0.01 | 0.01 | — |
| Carboxyvinyl Polymer | mass % | 0.5 | — | 0.5 | 0.5 | 0.5 |
| <Surfactant> | | | | | | |
| Polyglyceryl Laurate | mass % | — | 0.2 | — | — | — |
| <Iontophoretic Component> | | | | | | |
| Sodium Ascorbyl Phosphate | mass % | 0.1 | 0.1 | 0.1 | 0.1 | 0.1 |
| <Other Additives> | | | | | | |
| Bentonite | mass % | — | 0.15 | 0.15 | 0.15 | 0.15 |
| Methylparaben | mass % | 0.3 | 0.3 | 0.3 | 0.3 | 0.3 |
| Decamethylcyclopentasiloxane | mass % | — | 1 | — | — | — |
| Trioctyl Glyceryl | mass % | — | 2 | — | — | — |
| Cetyl 2-Ethylhexanoate | mass % | — | 2 | — | — | — |
| Polyoxyethylene · Methyl Polysiloxane Copolymer | mass % | — | 1.8 | 1.8 | 1.8 | 1.8 |
| Sodium Hydroxide | mass % | 0.01 | 0.02 | 0.02 | 0.02 | 0.01 |

TABLE 4

| | | Test Agent 17 | Test Agent 18 | Test Agent 19 | Test Agent 20 | Test Agent 21 |
|---|---|---|---|---|---|---|
| Appearance of Preparation | | A | C | A | C | C |
| Viscosity(mPa · s) | | 17800 | — | — | — | — |
| Ease of Attraction and Removel | 400 G | D | — | D | — | — |
| | 800 G | B | — | D | — | — |
| | 1200 G | B | — | D | — | — |
| | 2800 G | B | — | C | — | — |
| Residual Amount on Skin Surface | 400 G | D | — | D | — | — |
| | 800 G | B | — | D | — | — |
| | 1200 G | B | — | D | — | — |
| | 2800 G | B | — | D | — | — |

As is apparent from Table 1 to Table 4, test agents 1 to 9 and test agent 17 contain a specific amount of water as mentioned above, a specific amount of magnetic powder as mentioned above and a thickener. The magnetic powders contain a ferromagnetic ferrite as a main component and a mean volume particle diameter within a specific range as mentioned above. Owing to this, test agents 1 to 9 and test agent 17 are easily attracted and removed from a skin surface.

Test agents 1 to 9 and test agent 17 contain sodium ascorbyl phosphate. Sodium ascorbyl phosphate is ionized into ascorbyl phosphate ions and sodium ions in the test agents. Owing to this, as shown in FIG. 1, these test agents are attracted and removed from a skin surface; at the same time, ascorbyl phosphate ions (iontophoretic component 3) applied on the skin surface. Because of this, when a weak current flows through the skin surface after these test agents are attracted and removed, charged iontophoretic component 3 is mobilized toward the inside the skin to successfully perform infiltration of a beauty component into the skin. As a result, the beauty effect that the user can feel is likely to be improved.

The invention claimed is:
1. An aqueous skin care agent comprising:
    4 to 73 mass % of water;
    30 to 80 mass % of a magnetic granulated powder and has a mean volume particle diameter being 50 to 75 µm as determined from a particle size distribution obtained by a laser diffraction scattering method; a content of particles with a particle diameter being less than 37 μm of 15 mass % or less; and a content of particles with a particle diameter being 105 μm or more of 5 mass % or less; and a thickener, wherein the magnetic powder comprises a ferrimagnetic ferrite as a main component and a mean volume particle diameter being 20 to 100 μm as determined from a particle size distribution obtained by a laser diffraction scattering method.

2. The aqueous skin care agent according to claim 1, having a viscosity of 9000 mPas or more measured by a rotational viscometer with a rotational speed of 20 rpm, a temperature of 25° C. and for 60 seconds.

3. The aqueous skin care agent according to claim comprising 10 to 45 mass % of glycerin as the thickener.

4. The aqueous skin care agent according to claim 1, further comprising a thixotropic agent imparting thixotropy.

5. The aqueous skin care agent according to claim 1, further comprising a surfactant.

6. The aqueous skin care agent according to claim 1, wherein the magnetic powder comprises particles each having a resin film on the surface.

7. The aqueous skin care agent according to claim 1, wherein the magnetic powder has a chemical component comprising 80 mass % or more of a magnetite and a balance being wustite, hematite and inevitable impurities.

8. The aqueous skin care agent according to claim 1, wherein the magnetic powder has a saturation magnetization of 80 Am/kg or more measured with an integral type B-H tracer by a method comprising placing an H coil for measuring a magnetic field and a $4\pi I$ coil for measuring magnetization between electromagnets and the magnetite-based magnetic powder put in the $4\pi I$ coil; changing current values of the electromagnets to vary magnetic field H; separately integrating outputs from the H coil and the $4\pi I$ coil; plotting output from H coil on the X-axis and output from the $4\pi I$ coil on the Y-axis; drawing a hysteresis loop on a recording paper; and from the hysteresis loop calculating saturation magnetization, residual magnetization and magnetic coercive force; wherein the measuring for the hysteresis loop includes: sample amount of about 1 g, sample cell of 7 mmφ±0.02 mm in inner diameter and 10 mm±0.1 mm in height, the number of turns of $4\pi I$ coil of 30; applied magnetic field of 3000 oersteds.

9. The aqueous skin care agent according to claim 1, further comprising a charged iontophoretic component.

10. The aqueous skin care agent according to claim 6, wherein the resin film is an acrylates copolymer, a polyvinyl alcohol, a polyvinyl pyrrolidone, a methoxy ethylene-maleic anhydride copolymer, a cationic cellulose, a polyacrylic ester copolymer, or a methacrylic ester copolymer.

11. The aqueous skin care agent according to claim 6, wherein the resin film is an acrylates copolymer.

* * * * *